United States Patent
Kotary et al.

(10) Patent No.: US 7,244,398 B2
(45) Date of Patent: *Jul. 17, 2007

(54) DEVICE FOR DISPENSING A VOLATILE LIQUID USING A WICK IN AN AMBIENT AIR STREAM

(75) Inventors: Kara L. Kotary, Racine, WI (US); Padma Prabodh Varanasi, Racine, WI (US)

(73) Assignee: S. C. Johnson & Son, Inc., Racine, WI (US)

( * ) Notice: Subject to any disclaimer, the term of this patent is extended or adjusted under 35 U.S.C. 154(b) by 530 days.

This patent is subject to a terminal disclaimer.

(21) Appl. No.: 10/394,623

(22) Filed: Mar. 21, 2003

(65) Prior Publication Data

US 2004/0184969 A1 Sep. 23, 2004

(51) Int. Cl.
*A61L 9/00* (2006.01)

(52) U.S. Cl. ............... 422/124; 422/123; 239/34; 239/44; 239/49; 239/50

(58) Field of Classification Search ............... 422/123, 422/124; 239/34, 44, 49, 50; 222/187
See application file for complete search history.

(56) References Cited

U.S. PATENT DOCUMENTS

| | | | | |
|---|---|---|---|---|
| 1,129,897 A | * | 3/1915 | Owen, Jr. ............... | 239/45 |
| 1,911,871 A | | 5/1933 | Anderson | |
| 2,435,811 A | | 2/1948 | Waters ............... | 240/10 |
| 2,557,501 A | | 6/1951 | Fusay et al. ............... | 21/119 |
| 2,754,554 A | * | 7/1956 | Mills ............... | 422/121 |
| 2,764,789 A | | 10/1956 | Zelenka ............... | 21/74 |
| 2,828,953 A | | 4/1958 | Hartmann ............... | 261/30 |
| 2,867,866 A | * | 1/1959 | Steele ............... | 422/124 |

(Continued)

FOREIGN PATENT DOCUMENTS

AU 664685 11/1995

(Continued)

OTHER PUBLICATIONS

International Search Report and Written Opinion, Aug. 16, 2004, Appl. No. PCT/US04/008436.

(Continued)

*Primary Examiner*—Gladys J P Corcoran
*Assistant Examiner*—Sean E. Conley (57) ABSTRACT

A wick-based emanation device for dispensing a volatile liquid is disclosed. The dispensing device includes a housing and a fan mounted in the housing for generating an air stream used for dispersing the volatile liquid. Walls of the housing form an enclosure for mounting the fan and for receiving an exposed portion of the wick therein. A retention structure is provided for coupling the wick to the housing and securing the wick in the air stream generated by the fan. The volatile liquid migrates along the wick from the reservoir to the exterior of the container where it is evaporated from the surface of the wick by forced airflow generated by a motorized fan mounted in the housing. The wick is formed to have a width dimension W which does not exceed 1.2 times a dimension R of a blade of the fan extending from the fan axis of rotation to an edge of the fan blade farthest from the axis of rotation.

43 Claims, 4 Drawing Sheets

U.S. PATENT DOCUMENTS

| | | | | |
|---|---|---|---|---|
| 3,080,624 | A | 3/1963 | Weber, III | 21/120 |
| 3,550,853 | A * | 12/1970 | Gray | 239/44 |
| 3,587,968 | A | 6/1971 | Balland et al. | 239/47 |
| 3,633,881 | A | 1/1972 | Yurdin | 261/24 |
| 3,748,464 | A | 7/1973 | Andeweg | 240/108 R |
| 3,749,904 | A | 7/1973 | Graff | 240/10 B |
| 3,761,702 | A | 9/1973 | Andeweg | 240/2 R |
| 3,790,081 | A | 2/1974 | Thornton et al. | |
| 3,890,085 | A | 6/1975 | Andeweg | 431/125 |
| 3,923,458 | A | 12/1975 | Moran | 21/74 R |
| 3,948,445 | A | 4/1976 | Andeweg | 239/53 |
| 3,990,848 | A | 11/1976 | Corris | |
| 3,993,444 | A | 11/1976 | Brown | |
| 4,035,451 | A | 7/1977 | Tringali | |
| 4,166,087 | A | 8/1979 | Cline et al. | |
| 4,276,236 | A | 6/1981 | Sullivan et al. | |
| 4,294,778 | A | 10/1981 | DeLuca | |
| 4,323,193 | A | 4/1982 | Compton et al. | |
| 4,346,059 | A | 8/1982 | Spector | 422/125 |
| 4,383,951 | A | 5/1983 | Palson | |
| 4,432,938 | A | 2/1984 | Meetze, Jr. | |
| 4,493,011 | A | 1/1985 | Spector | 362/96 |
| 4,621,768 | A | 11/1986 | Lhoste et al. | 239/44 |
| 4,660,764 | A | 4/1987 | Joyaux et al. | 239/44 |
| 4,666,638 | A | 5/1987 | Baker et al. | |
| 4,695,435 | A | 9/1987 | Spector | |
| 4,707,338 | A | 11/1987 | Spector | |
| 4,739,928 | A | 4/1988 | O'Neil | |
| 4,743,406 | A | 5/1988 | Steiner et al. | |
| 4,857,240 | A | 8/1989 | Kearnes et al. | |
| 4,866,580 | A | 9/1989 | Blackerby | 362/205 |
| 4,913,350 | A | 4/1990 | Purzycki | 239/44 |
| 4,931,224 | A | 6/1990 | Holzner, Sr. | |
| 4,968,487 | A | 11/1990 | Yamamoto et al. | 422/125 |
| RE33,864 | E | 3/1992 | Steiner et al. | |
| 5,094,025 | A * | 3/1992 | Daniels | 43/1 |
| 5,095,647 | A | 3/1992 | Zobele et al. | 43/125 |
| 5,114,625 | A | 5/1992 | Gibson | |
| 5,126,078 | A | 6/1992 | Steiner et al. | |
| 5,133,042 | A | 7/1992 | Pelonis | |
| 5,217,696 | A | 6/1993 | Wolverton et al. | 422/121 |
| 5,222,186 | A | 6/1993 | Schimanski et al. | |
| 5,223,182 | A | 6/1993 | Steiner et al. | |
| 5,342,584 | A | 8/1994 | Fritz et al. | |
| 5,370,829 | A | 12/1994 | Kunze | |
| 5,376,338 | A | 12/1994 | Zlotnik | |
| 5,547,616 | A | 8/1996 | Dancs et al. | |
| 5,647,053 | A | 7/1997 | Schroeder et al. | |
| 5,651,942 | A | 7/1997 | Christensen | 422/125 |
| 5,662,835 | A | 9/1997 | Collingwood | |
| D386,974 | S | 12/1997 | Wefler | |
| D393,063 | S | 3/1998 | Wefler | |
| 5,891,400 | A | 4/1999 | Ansari et al. | 422/125 |
| 5,909,845 | A | 6/1999 | Greatbatch et al. | |
| 5,919,423 | A | 7/1999 | Requejo et al. | |
| 5,970,643 | A | 10/1999 | Gawel, Jr. | |
| 5,980,064 | A | 11/1999 | Metroyanis | 362/194 |
| 6,017,139 | A | 1/2000 | Lederer | 362/394 |
| 6,104,867 | A | 8/2000 | Stathakis et al. | 392/403 |
| 6,106,786 | A | 8/2000 | Akahoshi | 422/124 |
| 6,196,706 | B1 | 3/2001 | Cutts | 362/392 |
| 6,241,161 | B1 | 6/2001 | Corbett | |
| 6,354,710 | B1 | 3/2002 | Nacouzi | 362/96 |
| 6,361,752 | B1 | 3/2002 | Demarest et al. | 422/306 |
| 6,371,450 | B1 | 4/2002 | Davis et al. | |
| 6,416,242 | B1 | 7/2002 | Kaufmann | |
| 6,454,425 | B1 | 9/2002 | Lin | 362/96 |
| 6,484,438 | B2 | 11/2002 | Matsunaga et al. | 362/96 |
| 6,536,160 | B1 | 3/2003 | Morlier et al. | |
| 6,555,068 | B2 | 4/2003 | Smith | |
| 6,567,613 | B2 | 5/2003 | Rymer | |
| 6,616,308 | B2 | 9/2003 | Jensen et al. | 362/351 |
| 6,619,560 | B1 | 9/2003 | Chun | |
| 6,648,239 | B1 * | 11/2003 | Myny et al. | 239/44 |
| 6,766,817 | B2 | 7/2004 | da Silva | |
| 6,862,403 | B2 | 3/2005 | Pedrotti et al. | 392/395 |
| 6,899,280 | B2 * | 5/2005 | Kotary et al. | 239/34 |
| 6,938,883 | B2 | 9/2005 | Adams et al. | |
| 6,966,665 | B2 | 11/2005 | Limburg et al. | |
| 7,007,863 | B2 | 3/2006 | Kotary et al. | |
| 7,032,831 | B2 | 4/2006 | Duston et al. | |
| 2002/0080601 | A1 | 6/2002 | Meltzer | 362/96 |
| 2002/0093834 | A1 | 7/2002 | Yu et al. | 362/565 |
| 2002/0136542 | A1 | 9/2002 | He et al. | 392/395 |
| 2002/0136866 | A1 | 9/2002 | He et al. | 428/313.5 |
| 2003/0005620 | A1 * | 1/2003 | Ananth et al. | 43/125 |
| 2003/0007887 | A1 | 1/2003 | Roumpos et al. | 422/1 |
| 2003/0053305 | A1 | 3/2003 | Lin | 362/96 |
| 2003/0146292 | A1 | 8/2003 | Schramm et al. | |
| 2004/0065749 | A1 | 4/2004 | Kotary et al. | |
| 2004/0074982 | A1 * | 4/2004 | Kotary et al. | 239/44 |
| 2004/0141315 | A1 | 7/2004 | Sherburne | 362/161 |
| 2004/0182949 | A1 | 9/2004 | Duston et al. | |
| 2004/0184969 | A1 | 9/2004 | Kotary et al. | |
| 2004/0246711 | A1 | 12/2004 | Brenchley et al. | 362/161 |
| 2004/0257798 | A1 | 12/2004 | Hart | |
| 2004/0262419 | A1 | 12/2004 | Kotary et al. | |
| 2004/0262420 | A1 | 12/2004 | Hansen et al. | |
| 2004/0265189 | A1 | 12/2004 | Schwarz | |
| 2004/0265196 | A1 | 12/2004 | Varanasi et al. | 422/305 |
| 2005/0053528 | A1 | 3/2005 | Rymer | |

FOREIGN PATENT DOCUMENTS

| | | | |
|---|---|---|---|
| DE | 29907125 U1 * | 7/1999 | |
| DM | 054926 | 9/2000 | |
| EP | 0 882 459 | 12/1998 | |
| EP | 1 031 446 | 8/2000 | |
| EP | 1 270 021 | 1/2003 | |
| EP | 1 283 062 | 2/2003 | 9/3 |
| EP | 1 283 062 A1 | 12/2003 | |
| FR | 2 483 782 | 12/1981 | |
| GB | 2285579 | 7/1995 | |
| WO | WO 95/10352 | 4/1995 | |
| WO | WO 01/02025 A1 | 1/2001 | |
| WO | WO 01/23008 A1 | 4/2001 | |
| WO | WO 02/30220 A1 | 4/2002 | |
| WO | WO 02/31413 A2 | 4/2002 | |
| WO | WO 03/013618 | 2/2003 | |
| WO | EP 1 392 368 | 10/2003 | |
| WO | WO03/086487 | 10/2003 | |
| WO | WO 2004/030708 | 4/2004 | |

OTHER PUBLICATIONS

International Search Report and Written Opinion, Aug. 16, 2004, Appl. No. PCT/US04/008437.

"Inglow™ Candle Company" www.inglowcandle.com (2002).

"Luna Candles" http://www.epartyunlimited.com/luna-candles.html (print date 2005).

Office Action for U.S. Appl. No. 11/289,471 dated Apr. 26, 2006.

Office Action for U.S. Appl. No. 11/289,471 dated Oct. 16, 2006.

* cited by examiner

DEVICE FOR DISPENSING A VOLATILE LIQUID USING A WICK IN AN AMBIENT AIR STREAM

FIELD OF THE INVENTION

The present invention relates to emanation systems for volatile liquids and, more particularly, to a wick-based emanation system incorporating a fan mounted in a housing for dispersing the volatile liquid.

DETAILED DESCRIPTION OF THE INVENTION

Figure 1:
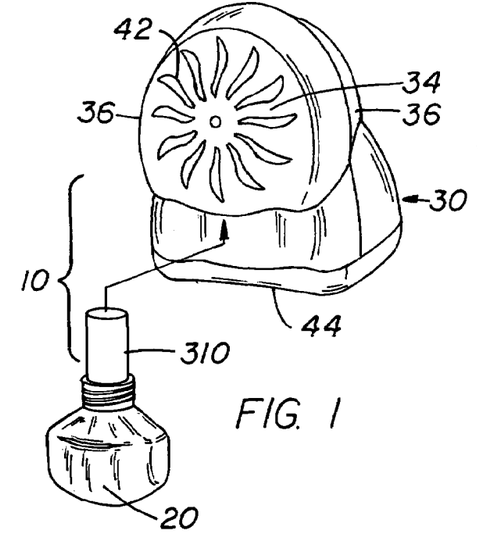
FIG. 1 is a perspective view showing insertion of a wick into a housing of a dispensing device of the present invention.
Figure 2:
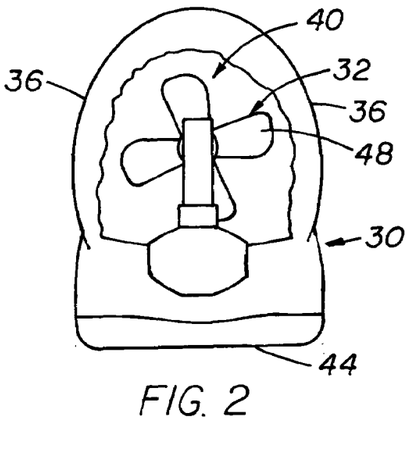
FIG. 2 is a front view of the dispenser of FIG. 1 showing the dispenser housing partially cut away with the wick positioned in the housing.
Figure 3:
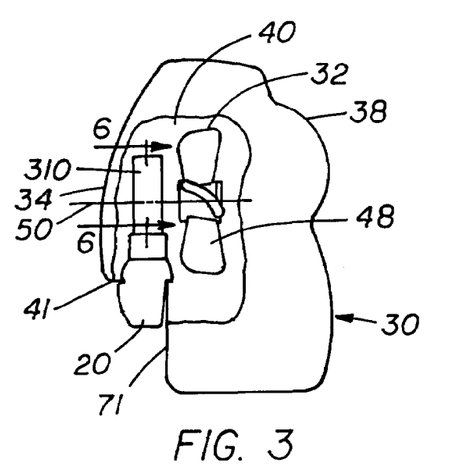
FIG. 3 is a side view showing the dispenser housing partially cut away with the wick positioned in the housing as shown in FIG. 2.

Referring to FIGS. 1-3, volatile liquid dispenser 10 is designed to disseminate a volatile liquid, such as a fragrance compound, into a room. The fragrance compound is disseminated via a forced air stream flowing around a wick 310 at room ambient temperature. According to the present invention, dispenser 10 includes a housing 30, a motorized fan 32 mounted in housing 30 for generating an air stream, and a wick 310 coupled to housing 30. Housing 30 includes a front wall 34, a side 36 formed at each lateral end of front wall 34, and a rear wall 38 formed opposite front wall 34. Front wall 34, sides 36, and rear wall 38 combine to form an enclosure 40 for housing fan 32 and for receiving wick 310 into the air stream generated by fan 32. One or more air inlet ports (not shown) may be formed in rear wall 38 for providing intake air for fan 32. Also, one or more air outflow ports 42 are provided in front wall 34 to provide a path for outflow of the air stream from enclosure 40. A lower portion of housing 30 forms a base 44 configured to enable dispenser 10 to rest on a flat surface. A switch or button (not shown) may be provided on an exterior surface of housing 30 to enable activation and deactivation of the fan motor.

Figure 4:
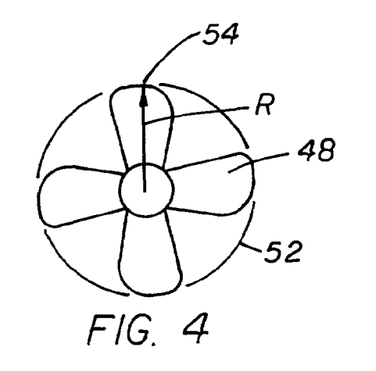
FIG. 4 is a front view of a fan blade assembly mounted in the dispenser housing as shown in FIG. 2.
Figure 6:
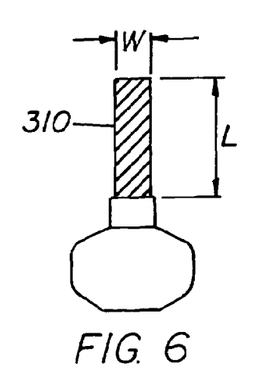
FIG. 6 is a cross-sectional view of the wick of FIG. 3 taken along a length of the wick.

Referring to FIGS. 3, 4 and 6, fan 32 is powered by a battery (not shown) positioned in base 44 of housing 30. Access to the battery may be provided by a hinged or removable access plate formed in base 44. Fan 32 includes a plurality of fan blades 48 that rotate about a fan axis of rotation 50 during operation of the fan. During rotation, fan blades 48 trace out a circumferential path 52. As shown in FIG. 4, fan blades 48 each have a dimension R extending from axis of rotation 50 to an edge 54 of the respective fan blade 48 farthest from axis of rotation 50.

Referring to FIG. 2, in the present invention the size of a profile of wick 310 immersed in the air stream is controlled relative to the size of fan 32 used to generate the air stream. To accomplish this, wick 310 is formed to have a width dimension W, as shown in FIG. 6, which does not exceed 1.2 times the dimension R (FIG. 4) extending from axis of rotation 50 to the edge 54 of any fan blade 48 farthest from axis of rotation 50. In the embodiment shown, R=21.15 mm and W=12.7 mm. Width dimension W may be measured transverse to rotational axis 50 of the fan. Width dimension W may also be measured transverse to a length dimension of wick 310.

In alternative embodiments, wick 310 may be formed to have a width dimension W which does not exceed 80 times the dimension R, 0.60 times the dimension R, etc.

Referring now to FIGS. 1 and 7-10, wick 310 is to be positioned and secured in enclosure 40 formed by housing 30 and so as to reside in the air stream generated by fan 32. Wick 310 may be secured in the desired position by coupling wick 310 to dispenser housing 30 using any one of numerous methods.

Referring to FIGS. 1-3, in one embodiment wick 310 may be secured in a container 20 holding the volatile liquid to be dispensed. A portion of wick 310 is in communication with the volatile liquid in container 20. Another portion of wick 310 extends outside container 20 for immersion into the air stream.

Referring to FIGS. 3 and 5, in one embodiment, wick 310 is secured in a container 20 holding the volatile liquid. A portion of wick 310 extends into an interior of container 20 to contact the volatile liquid. Referring to FIG. 3, dispenser housing 30 has opposing sidewalls 41 and 71. Each of opposing sidewalls 41 and 71 has a corresponding edge portion 52 and 54, respectively. Edge portions 52, 54 define an opening adapted to receive wick 310 and a portion of container 20 into enclosure 40. A retention structure is formed along one or more of opposing sides of container 20 to help position and releasably secure container 20 between opposing sidewalls 41 and 71 of housing 30. The retention structure may be formed integral with container 20. When container 20 is secured to dispenser housing 30 as described above, wick 310 is positioned in the air stream generated by fan 32. As seen in FIGS. 2 and 3, when wick 310 is in its desired position within enclosure 40, wick is spaced apart from any interior surface of housing 30. Also, as seen in FIGS. 2 and 3, wick 310 may be positioned along the fan rotational axis 50.

In an alternative embodiment (not shown), a receptacle for wick 310 may be formed on dispenser housing 30 for placement of wick 310 directly therein. The receptacle would be positioned on dispenser housing 30 such that a wick received therein resides in an air stream generated by fan 32 as described above.

Examples of other retention structures suitable for the purpose described above are disclosed in co-pending patent application entitled "Container For A Device For Dispensing Volatile Liquid", incorporated herein by reference, and filed Mar. 21, 2003.

As stated previously, the volatile liquid migrates along wick 310 from the reservoir to the exterior of container 20 where it is evaporated from the surface of wick 310 by forced airflow generated by a motorized fan mounted in housing 100. Detailed descriptions of some representative wick structures which may be incorporated into the dispenser of the present invention are provided in co-pending patent applications having U.S. Ser. Nos. 10/266,512; 10/266,798; and 10/266,546 and are incorporated herein by reference.

Figure 10:
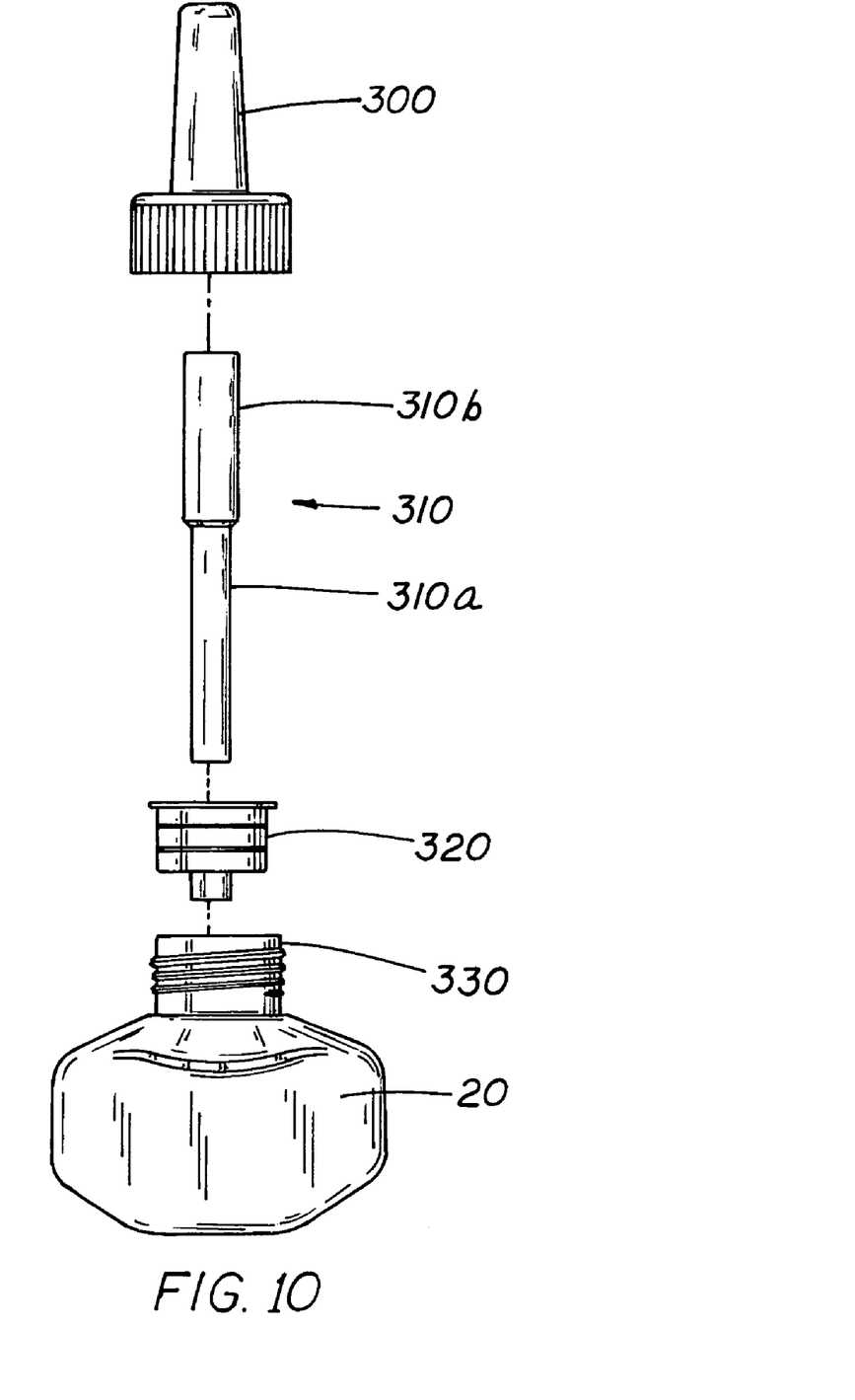
FIG. 10 is an exploded view of a wick secured in a container as seen in FIG. 1.

Referring to FIG. 10, a portion of wick 310 that is co-extensive with neck 330 of container 20 is shaped so that it fits snugly into the neck 330 of the container 20. The wick 310 is long enough so that its bottom surfaces come into contact with the liquid in the container 20 and its top surfaces are exposed to the ambient air. (The level of the liquid is not shown in the container 20.) It is preferable to use a neck closure 320, such as that shown in FIG. 10, to hold the wick 310 in place and to prevent leakage around the neck 330 of the container 20. The fit between the neck closure 320 and the container 20 is tight enough to prevent leakage of the liquid from the container 20. Likewise, the fit between the neck closure 320 and the wick 310 is sufficiently tight to prevent leakage of the liquid from the container 20.

In addition, the neck 330 of the container 20 may be shaped so that a cover 300 can be securely fastened over the wick 310 and neck closure 320. For example, the outer neck 330 of the container 20 may be threaded so that cover 330 can be screwed on top of the container 20 when the device is not in use.

Referring again to FIG. 10, the container 20 and the neck closure 320 can be made of any suitable material that is leakproof and adaptable to incorporate the characteristics of the retention structure embodiments described herein. The size of the opening in the container 20 and the size of the neck closure 320 are dependent upon each other and upon the size of the wick 310 that is to be used with the device.

The neck closure 320 or neck 330 of the container 20 may be formed with a small hole (e.g., a vent-hole) to help counter the effects of a vacuum that can form in the head-space of the container 20. The wick 310 transports the liquid to the surface of the wick 310 by a principle called capillary action. In particular, the wick material contains numerous pores, and these pores act as capillaries, which cause the liquid to be drawn into them. As the liquid is drawn from the container and transported up the porous wick 310, a vacuum is created in the head-space of the container 20. The formation of a vacuum in the head-space of the container 20 decreases the rate that the liquid is wicked from the reservoir to the surface. This decrease in the wicking rate translates directly into a decrease in the release rate of the liquid to the ambient air. Accordingly, in order to combat the formation of the vacuum in the head-space, it is often preferable to form a vent-hole in the vicinity of the head-space of the container 20. However, if the container 20 is overturned, either during shipping or, later, during handling of the bottle by the consumer, it is possible for the concentrated liquid in the container 20 to leak out of the vent-hole. Therefore, if is preferable to design a device that does not require a vent-hole.

It has been found that if the pore size of the wick 310 is below a critical size, the vent-hole can be eliminated without sacrificing the release rate of the vaporizable liquid into the ambient air. Because the capillary force increases as the pore size of the wick 310 decreases, a wick 310 with very small porosity has a very strong capillary force. This strong capillary force allows the wick 310 to continue to be able to transport the liquid from the container 20 to the surface of the wick 310 even though a vacuum has formed in the head-space of the container 20. In other words, a wick 310 with a very small pore size is able to overcome the vacuum effect that is present in the head-space of the container 20.

The critical size of the wick 310 is determined by the surface tension of the liquid, the compatibility of the wick 310 and liquid (i.e., the contact angle), and the extent to which a vacuum is generated with the head-space of the container 20. In particular, we have found that if the wick 310 is manufactured with a mean pore size that is below about four microns, the effects of a vacuum in the head-space of the container 20 can be greatly decreased. Specifically, we have found that it is most preferable that the mean pore size of the wick 310 be below about one micron. When the wick 310 has a mean pore size of below four microns, and preferably below one micron, we have found that the wick 310 is still able to effectively function to transport the liquid from the container 20 to the surface of the wick 310.

When using a device of this invention, it is not necessary to provide a vent-hole in the upper part of the container 20, or in the neck closure 320 because the vacuum effects are substantially decreased. By eliminating the vent-hole, the problem of spillage or leakage that occurs as a result of the existence of the vent-hole is also eliminated.

The mean pore size of the wick 310 can be determined by any standard test for determining porosity and pore size distribution. For example, mercury porosimetry is a method that gives information on porosity and pore size distribution for rigid wicks. It is based on the measurement of differential increments in the amount of mercury intruded into the wick 310 as a function of increasing applied pressure.

It has also been found that another advantage in using a wick 310 with a mean porosity of below about four microns, and preferably below about one micron, is that the lower porosity decreases the likelihood of the liquid spilling or leaking through the wick 310 itself. Since the upper surface of the wick 310 is exposed to the ambient air, if the container 20 is overturned, it is possible for liquid to leak out through a wick of conventional pore sizes. Using a smaller porosity wick 310 of this invention, however, decreases the ability of the liquid to travel through the wick 310 when the container 20 is overturned.

The wick 310 can be made of a variety of materials. It is preferable that the wick 310 be rigid enough to provide minimal contact area with the surface that the wick 310 comes in contact with. Polymeric wicks, for example, have been found to be effective for these purposes. In particular, wicks composed of ultra high molecular weight, high density polyethylene (HDPE) have been found to be suitable. Such wicks are generally comprised of blends of HDPE in particle form, and the blends are developed to meet the target pore characteristics of the wick 310.

Preferably, the solubility parameter of the polymer used in the wick 310 is significantly different from that of any of the components contained in the liquid. This prevents the wick 310 from swelling (or other changes) that may lead to a change in the pore size and porosity of the wick 310, which would consequently affect the release rate of the vaporizable liquid into the ambient air.

The wick 310 can also be made in a variety of shapes. FIG. 10, for example, shows a cylindrical wick 310 with a narrower lower region. This change in shape of the wick 310 is not required. Instead, this variation in shape can be useful in that it both increases the amount of the surface area of the wick 310 that is exposed to the ambient air and aids in forming a tighter seal at the neck 330 area of the container 20, thus helping to prevent spilling or leaking of the liquid from the container 20. The above-described benefits of using a wick 310 with a mean pore size of below about four microns, and preferably below about one micron, can be obtained with wicks of many different shapes.

Figure 5:
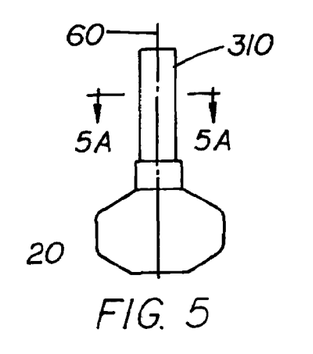
FIG. 5 is a front view of the wick secured in a container for insertion into the housing of the dispensing device as shown in FIG. 1.
Figure 5A:
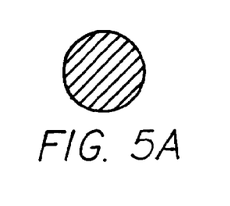
FIG. 5A is a cross sectional view of the wick of FIG. 5 taken along line 5A-5A transverse to a length of the wick.

Referring to FIGS. 5 and 5A, it may be seen that wick 310 is elongate and has a longitudinal axis 60. It may also be seen that a cross section (FIG. 5A) of the wick transverse to longitudinal axis 60 has a perimeter that is generally circular in shape. In alternative embodiments (not shown), wick 310 may be constructed such that the perimeter of the cross section of wick 310 transverse to longitudinal axis 60 has any one of several geometric shapes. For example, the shape of the perimeter of the wick cross section may be hexagonal, rectangular, triangular, elliptical, etc. The ability to form a wick having any of a variety of cross-sectional shapes provides an additional method for controlling the surface area of the wick to be immersed in the airflow.

Figures 7, 7A:
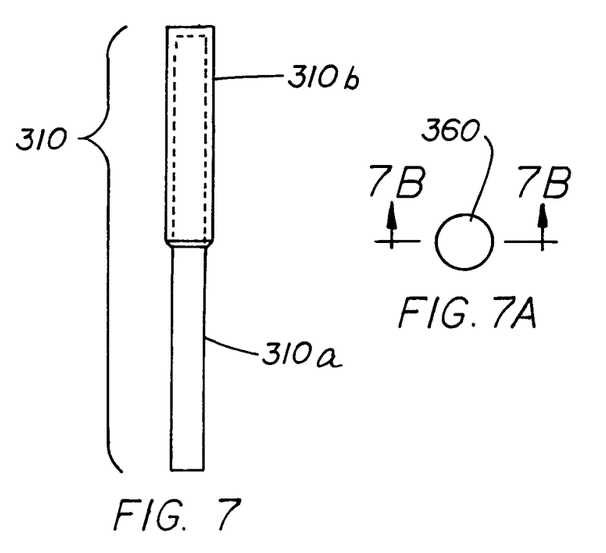
FIG. 7 is a side view of an embodiment of the wick.
FIG. 7A is a top view of the wick of FIG. 7.
Figure 7B:
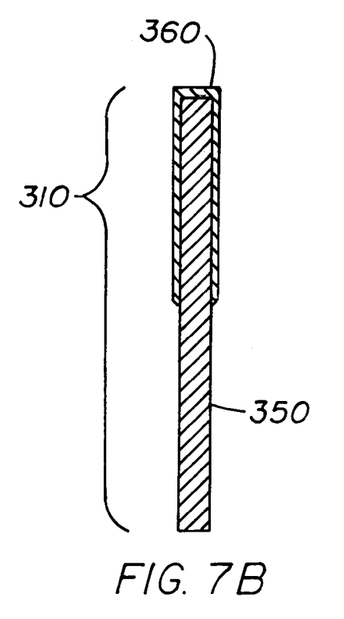
FIG. 7B is a cross-sectional view of the wick of FIG. 7A taken along line B-B in FIG. 7A.
Figure 8A:
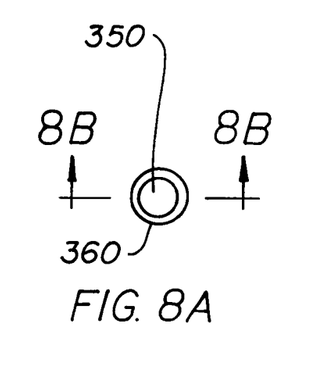
FIG. 8A is a top view of another embodiment of the wick.
Figure 8B:
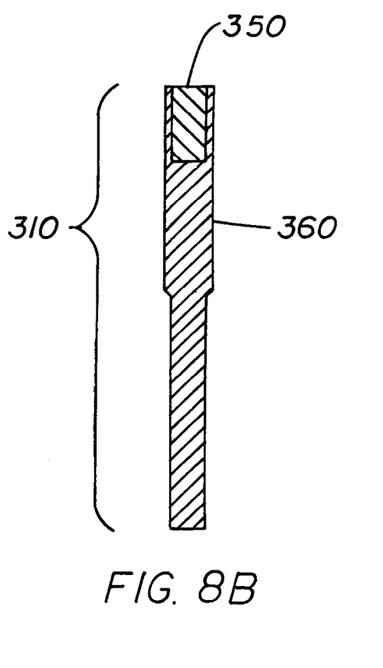
FIG. 8B is a cross-sectional view of the wick of FIG. 8A taken along line A-A in FIG. 8A.
Figure 9A:
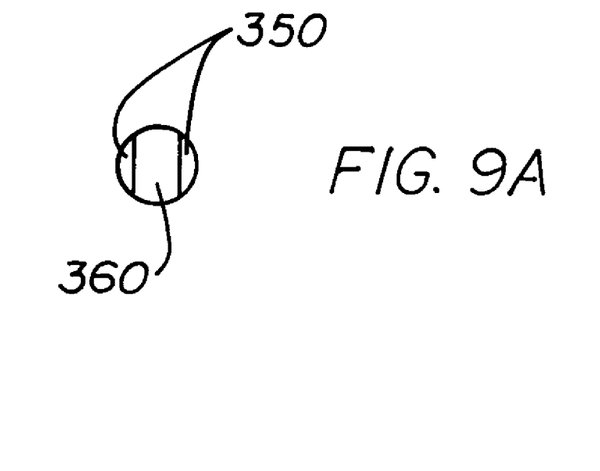
FIG. 9A is a top view of still another embodiment of the wick.
Figure 9B:
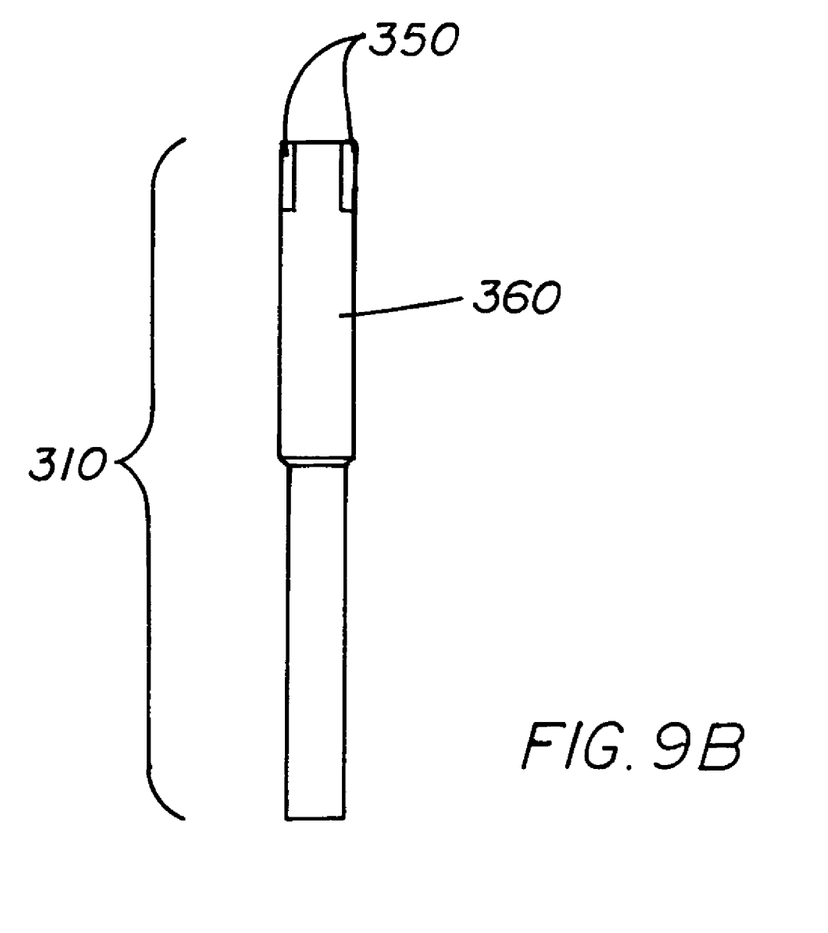
FIG. 9B is a side view of the wick in FIG. 9A.

As shown in FIG. 7, it is also possible to provide a wick 310 with an outer layer that is made up of a material with larger pore sizes. In FIG. 7, the large pore outer section 310*b* completely surrounds the exposed portion of the wick 310*a*. The small pore size section 310*a* extends into the container 20 and is in contact with the liquid. In this manner, the smaller pores of the inner portion 310*a* of the wick 310 allow the delivery system to be constructed without a vent-hole, while the larger pores of the outer portion 310*b* provide a maximum release rate of the vaporizable liquid off the surface of the wick 310 that is exposed to the ambient air. It should be noted, however, that the large pore section 310*b* need not completely surround the upper region of the small pore section 310*a* as shown in FIG. 7 in order to provide the benefits of this invention.

It is often desired that the volatile liquid dispenser described herein exhibit an initial spike in the release rate of the volatile liquid when the device is first activated. For example, when a fragrance dispensing device is activated, an initial spike in the release rate of the volatile liquid fragrance compound is desired in order to quickly disperse into the air a sufficient amount of the fragrance compound to effectively decrease the number of insects in the surrounding area. Once an optimum level of fragrance compound is present in the ambient air of the operating area, however, the release rate of the fragrance compound should be decreased to an amount that is sufficient to maintain that optimum level. By having two sections of varying pore size exposed to the ambient air at the same time, it is possible to achieve an initial spike effect.

Referring to FIGS. 7A, 7B, 8A, 8B, 9A and 9B, in various embodiments of the wick, the initial spike effect described above may be achieved by having a wick 310 that is comprised of at least two sections. A first section 350 is made of a material that has a predetermined pore size, while the second section 360 is made of a material that has a pore size that is greater than that of the material of the first section. Both sections of the wick are exposed to the ambient air.

In the wick embodiments described above, the cylindrical shape of the large pore section 360 is also narrowed at its lower portion. The pore size of the lower portion of large pore section 360, however, does not change with this change in diameter. Importantly, this change in shape is not required for achieving the initial spike effect. Instead, this variation in shape can be useful in that it both increases the amount of the surface area exposed to the ambient air and aids in forming a tighter seal at the neck 330 area of the container 20 (FIG. 10), thus helping to prevent spilling or leaking of the liquid from the container 20.

In the above-described embodiments, the wick is longitudinal, has a longitudinal axis and a curved exterior surface. In alternative embodiments, the wick may be formed such that a cross-section of the wick taken perpendicular to the longitudinal axis has any one of a variety of simple geometric shapes, such as a circle, a diamond, a rectangle, a hexagon, an octagon, an oval or a triangle.

INDUSTRIAL APPLICABILITY

The present invention provides a structure and method for controlling the size of a profile of a wick immersed in an air stream relative to the size of a fan used to generate the air stream. This allows the resistance to the air stream produced by the wick to be minimized. When combined with the positioning of the wick within the air stream, this enables the linear velocity of the air flowing around the wick to be maximized, thereby ensuring rapid and efficient dissemination of a volatile substance drawn through the wick from a reservoir.

It should be understood that the preceding is merely a detailed description of various embodiments of this invention and that numerous changes to the disclosed embodiment can be made in accordance with the disclosure herein without departing from the spirit or scope of the invention. The preceding description, therefore, is not meant to limit the scope of the invention. Rather, the scope of the invention is to be determined only by the appended claims and their equivalents.

The invention claimed is:

1. A dispenser for a volatile liquid, comprising:

a fan mounted to a housing for generating an air stream; and a portion of substantially rigid wick positioned to be immersed in an air stream generated by the fan, wherein the wick includes a first capillary section and a second capillary section, wherein the second capillary section comprises an outer layer of porous wicking material that surrounds at least a portion of the surface of the first capillary section of the wick that is positioned to be immersed in the air stream, wherein the outer layer has a predetermined mean pore size that is greater than a mean pore size of the first capillary section of the wick.

2. The dispenser of claim 1 wherein the wick has a longitudinal axis and a cross section of the wick transverse to the longitudinal axis has a perimeter that defines a simple geometric shape.

3. The dispenser of claim 2 wherein the perimeter of the wick crass section is rectangular.

4. The dispenser of claim 2 wherein the perimeter of the wick cross section is square.

5. The dispenser of claim 1 wherein a portion of the wick is in communication with the volatile liquid.

6. The dispenser of claim 2 wherein the perimeter of the wick cross section is hexagonal.

7. The dispenser of claim 2 wherein the perimeter of the wick cross section is circular.

8. The dispenser of claim 2 wherein the perimeter of the wick cross section is elliptical.

9. The dispenser of claim 2 wherein the perimeter of the wick cross section is triangular.

10. The dispenser of claim 1 in which the portion of the wick positioned to be immersed in the air stream includes both the first and second capillary sections.

11. The dispenser of claim 1 in which the first capillary section is formed having a predetermined pore size and the second capillary section is formed having a predetermined pore size that is greater than the pore size of the first capillary section.

12. The dispenser of claim 11 wherein the ratio of the pore size of the second capillary section to that of the first capillary section is greater than approximately two.

13. The dispenser of claim 1 wherein the first capillary section is formed on top of the second capillary section.

14. The dispenser of claim 1 wherein each of the first capillary section and the second capillary section is cylindrical in shape.

15. The dispenser of claim 1 wherein the wick has a curved exterior surface.

16. The dispenser of claim 1 wherein the wick has a predetermined mean pore size of less than about four microns.

17. The dispenser of claim 1 wherein the outer layer completely surrounds the surface of the first capillary section of the wick that is positioned to be immersed in the air stream.

18. The dispenser of claim 1 wherein the first capillary section of the wick has a predetermined mean pore size of less than about one micron.

19. The dispenser of claim 1 wherein the wick is positioned along an axis of rotation of the fan.

20. The dispenser of claim 1 wherein the wick is spaced apart from any interior surface of the housing.

21. The dispenser of claim 1, further comprising a blade of the fan having a dimension R extending from an axis of rotation of the fan blade to an edge of the fan blade farthest from the axis of rotation, wherein the wick has a width W which does not exceed 1.2R.

22. The dispenser of claim 21 wherein the wick is elongate.

23. The dispenser of claim 22 wherein the wick has a longitudinal axis and the width W is measured transverse to the longitudinal axis of the wick.

24. The dispenser of claim 21 wherein the wick has a length and the width W is measured transverse to the length of the wick.

25. The dispenser of claim 24 wherein the width W is measured transverse to an axis of rotation of the fan.

26. The dispenser of claim 25 wherein width W does not exceed R.

27. The dispenser of claim 25 wherein width W does not exceed 0.8R.

28. The dispenser of claim 25 wherein width W does not exceed 0.6R.

29. The dispenser of claim 25 wherein width W does not exceed 0.4R.

30. The dispenser of claim 25 wherein width W does not exceed 0.2R.

31. A method for assembling a dispenser for a volatile liquid, comprising the steps of:
providing a fan mounted to a housing for generating an air strewn in which a blade of the fan has a dimension R extending from an axis of rotation of the fan blade to an edge of the fan blade farthest from the axis of rotation; and
positioning a substantially rigid wick to be immersed in an air strewn generated by the fan in which the wick has a width W which does not exceed 1.2 R, and wherein the wick includes a first section and a second section comprising an outer layer of porous wicking material that surrounds at least a portion of the surface of the first section that is positioned to be immersed in the air stream, wherein the outer layer has a predetermined mean pore size that is greater than a mean pore size of the first section.

32. The method of claim 31 in which the step of positioning includes providing a wick with the width W which does not exceed R.

33. The method of claim 31 in which the step of positioning includes providing a wick with the width W which does not exceed 0.8 R.

34. The method of claim 31 in which the step of positioning includes providing a wick with the width W which does not exceed 0.6 R.

35. The method of claim 31 in which the step of positioning includes providing a wick with the width W which does not exceed 0.4 R.

36. The method of claim 31 in which the step of positioning includes providing a wick with the width W which does not exceed 0.2 R.

37. The method of claim 31 in which the step of positioning includes providing a wick having a perimeter of a cross section of the wick taken transverse to a length of the wick to include one of a rectangle, square, hexagon, octagon, circle, ellipse and a triangle.

38. The method of claim 31 in which the step of positioning includes positioning the wick along the axis of rotation of the fan.

39. The method of claim 31 in which the step of positioning includes positioning the wick spaced apart from an interior surface of the housing.

40. The dispenser of claim 1, wherein the wick comprises high density polyethylene.

41. A dispenser for a volatile liquid, comprising: a housing; a container for holding the volatile liquid carried by the housing; a fan carried by the housing; and a rigid wick carried by the container, the wick comprising a first capillary section of porous wicking material having a first mean pore size, a bottom end in contact with the volatile liquid, and a top end disposed outside of the container, and the wick further comprising a second capillary section of porous wicking material having a second mean pore size and surrounding the top end of the first section; wherein the second mean pore size is greater than the first mean pore size; and wherein the second capillary section is positioned inside the housing to be immersed in an air stream generated by the fan.

42. The dispenser of claim 41, wherein the wick comprises high density polyethylene, and wherein the first mean pore size is less than about two microns and the first capillary section prevents leakage of the volatile liquid out of the container.

43. The dispenser of claim 41, wherein the fan comprises a blade having a dimension R extending from an axis of rotation of the blade to an edge of the blade farthest from the axis of rotation, wherein the wick has a maximum width W defined transverse to a longitudinal axis thereof, wherein the width W is less than 1.2 R, and wherein the longitudinal axis of the wick is aligned with the axis of rotation of the fan.

* * * * *

UNITED STATES PATENT AND TRADEMARK OFFICE
CERTIFICATE OF CORRECTION

| | |
|---|---|
| PATENT NO. | : 7,244,398 B2 |
| APPLICATION NO. | : 10/394623 |
| DATED | : July 17, 2007 |
| INVENTOR(S) | : Kara L. Kotary and Padma Prabodh Varanasi |

Page 1 of 1

It is certified that error appears in the above-identified patent and that said Letters Patent is hereby corrected as shown below:

Column 6, Line 39: insert --a-- after "of"

Column 6, Line 55: replace "crass" with --cross--

Column 7, Line 61: replace "strewn" with --stream--

Column 7, Line 66: replace "strewn" with --stream--

Signed and Sealed this

Twenty-seventh Day of January, 2009

JOHN DOLL
*Acting Director of the United States Patent and Trademark Office*